(12) United States Patent
Medoff

(10) Patent No.: US 11,986,227 B2
(45) Date of Patent: May 21, 2024

(54) METHOD AND APPARATUS FOR MAINTAINING A POSITION OF A BONE FRAGMENT IN RELATIONSHIP TO ANOTHER BONE PART

(71) Applicant: TriMed Inc., Santa Clarita, CA (US)

(72) Inventor: Robert Medoff, Kailua, HI (US)

(73) Assignee: TriMed Inc., Santa Clarita, CA (US)

( * ) Notice: Subject to any disclaimer, the term of this patent is extended or adjusted under 35 U.S.C. 154(b) by 419 days.

(21) Appl. No.: 17/152,253

(22) Filed: Jan. 19, 2021

(65) Prior Publication Data

US 2021/0220031 A1 Jul. 22, 2021

Related U.S. Application Data

(60) Provisional application No. 62/963,330, filed on Jan. 20, 2020.

(51) Int. Cl.
*A61B 17/80* (2006.01)

(52) U.S. Cl.
CPC ........ *A61B 17/809* (2013.01); *A61B 17/8004* (2013.01); *A61B 17/8052* (2013.01)

(58) Field of Classification Search
CPC . A61B 17/0642; A61B 17/68; A61B 17/8004; A61B 17/809; A61B 17/842; A61B 17/848
See application file for complete search history.

(56) References Cited

U.S. PATENT DOCUMENTS

| | | | |
|---|---|---|---|
| 1,130,378 | A | 3/1915 | Collis |
| 2,501,978 | A | 3/1950 | Wichman |
| 5,352,229 | A | 10/1994 | Goble et al. |
| 5,709,682 | A | 1/1998 | Medoff |
| 5,718,706 | A | 2/1998 | Roger |
| 5,779,707 | A | 7/1998 | Bertholet et al. |
| 5,941,878 | A | 8/1999 | Medoff |
| 5,961,521 | A | 10/1999 | Roger |
| 6,113,603 | A | 9/2000 | Medoff |
| 6,432,140 | B1 | 8/2002 | Lin |
| 7,037,308 | B2 | 5/2006 | Medoff |
| 7,731,718 | B2 | 6/2010 | Schwammberger et al. |
| 7,811,286 | B2 | 10/2010 | Medoff |

(Continued)

FOREIGN PATENT DOCUMENTS

| | | |
|---|---|---|
| CN | 209 529 310 U | 10/2019 |
| GB | 2 451 187 A | 1/2009 |

OTHER PUBLICATIONS

International Preliminary Report on Patentability and Written Opinion of the International Searching Authority, dated Jul. 26, 2022 in International Patent Application No. PCT/US2021/013938.

(Continued)

*Primary Examiner* — Larry E Waggle, Jr.

(74) *Attorney, Agent, or Firm* — Wood, Phillips, Katz, Clark & Mortimer

(57) ABSTRACT

A method and apparatus for maintaining a position of a first bone part relative to a second bone part. The apparatus has a unitary body made up of at least one elongate formed wire component and a base. A fastener is used to anchor the base to one of the bone parts to thereby maintain the apparatus in an operative position wherein at least a portion of the one elongate formed wire component engages at least the other bone part.

11 Claims, 7 Drawing Sheets

(56) References Cited

U.S. PATENT DOCUMENTS

| | | |
|---|---|---|
| 7,942,301 B2 | 5/2011 | Sater |
| 7,942,877 B2 * | 5/2011 | Medoff ................. A61B 17/68 |
| | | 606/103 |
| 7,988,691 B2 | 8/2011 | Schulze et al. |
| 8,235,995 B2 | 8/2012 | Focht et al. |
| 8,287,543 B2 | 10/2012 | Medoff |
| 8,337,528 B2 | 12/2012 | Ferree |
| 8,475,504 B2 * | 7/2013 | Gillard ............... A61B 17/8061 |
| | | 606/301 |
| 8,617,214 B2 | 12/2013 | Malek |
| 8,795,277 B2 | 8/2014 | Leuenberger et al. |
| 9,427,232 B2 | 8/2016 | Gupta et al. |
| 9,433,452 B2 | 9/2016 | Weiner et al. |
| 9,603,597 B2 | 3/2017 | Gupta et al. |
| 9,737,337 B2 | 8/2017 | Ferree |
| 10,004,603 B2 * | 6/2018 | Appenzeller ...... A61B 17/8085 |
| 2006/0189992 A1 | 8/2006 | Medoff |
| 2007/0233113 A1 | 10/2007 | Kaelblein et al. |
| 2008/0077132 A1 * | 3/2008 | Medoff ................ A61B 17/842 |
| | | 606/232 |
| 2014/0012316 A1 | 1/2014 | Stupak |
| 2014/0058510 A1 | 2/2014 | Appenzeller et al. |
| 2016/0367298 A1 | 12/2016 | Weiner et al. |
| 2018/0263778 A1 | 9/2018 | Appenzeller et al. |
| 2019/0357953 A1 | 11/2019 | Venturini et al. |
| 2020/0008846 A1 | 1/2020 | Medoff |

OTHER PUBLICATIONS

Extended European Search Report dated Apr. 25, 2023 in European Patent Application No. EP 21 74 4471.

* cited by examiner

METHOD AND APPARATUS FOR MAINTAINING A POSITION OF A BONE FRAGMENT IN RELATIONSHIP TO ANOTHER BONE PART

BACKGROUND OF THE INVENTION

Field of the Invention

This invention relates to medical implants and, more particularly, to a method and apparatus used to maintain a desired relationship between separate bone parts, such as a bone fragment and another stabilizing bone part.

Background Art

Many different implants have been devised to maintain a desired position of a bone fragment in relationship to another bone part, which may be an uncompromised stable bone part or another intermediate fragment. For simplicity, maintenance of a relationship between a bone fragment and a "stable" bone part will be focused upon herein only as a representative practicing of the invention. However, the invention more generically relates to controlling a relationship between any separate bone parts.

One category of this type of implant uses a formed wire arrangement that is fixed to a stable bone part. The wire portion generally either captively holds a separated bone fragment in a desired relationship or provides a foundation upon which a "bone fragment" can be effectively constructed.

For purposes of simplicity throughout the background, description, and claims herein, a "formed elongate component or wire" will be used generically to encompass an actual wire, a pin, and any other like elongate component that is strategically shaped to function as other than a straight piece or fastener. For each implant, the wire is shaped to accomplish a specific task, based upon the particular anatomy—including the particular bone that is stable and the nature of the fragment to be maintained in a desired relationship therewith. Currently, such wires are commonly made from 0.045" to 0.090" diameter material, though other gauges are utilized.

The Applicant herein makes a number of such implants, certain of which have been arbitrarily identified as "sled" implants, with others characterized as buttressing devices. A number of such representative apparatus are disclosed in the following patents, assigned to the Applicant herein: U.S. Pat. No. 5,709,682 ("Surgical Clamp For Fixation Of Bone Fragments"); U.S. Pat. No. 5,941,878 ("Implantable Surgical Buttressing Device"); U.S. Pat. No. 6,113,603 ("Graft Constraint Device"); U.S. Pat. No. 7,037,308 ("Implant Device For Applying Compression Across A Fracture Site"); U.S. Pat. No. 7,811,286 ("Implant Device For Applying Compression Across A Fracture Site"); and U.S. Pat. No. 8,287,543 ("Fracture Fixation System Including Buttress Pin And Post Washer").

The diameter of the wires can be constant or non-uniform. In a typical configuration, the wire has a proximal U-shaped portion that is fixed to a stable bone part and extends to one or more legs, each with a free end. In some configurations, the U-shaped portion has a smaller gauge to facilitate formation, with the legs having a larger gauge for strength and rigidity.

Heretofore, these wire forms have been secured to bone by applying a washer or small plate, hereinafter generically identified as a "washer". The washer is placed on the wire surface to sandwich the implant between the undersurface of the washer and the underlying bone.

While this construction has been functional, there are a number of undesirable features inherent with this design. First, it is somewhat awkward and inconvenient for a surgeon to have to handle separate pieces—in this case the washers, fasteners, and implant body—during a procedure. A surgeon must coordinate the handling of the pieces to allow fastener-accommodating holes to be drilled into the bone. In the case of a small diameter wire, a commonly used washer is proportionately small and difficult to handle, and thus prone to being dropped during a procedure—which, aside from the inconvenience, creates the potentially difficult task of recovering and repositioning the same. For example, one known washer has been designed to be quite small to ensure that it does not cover a large surface of bone and thereby limit screw placement from an opposite side. However, it is easy for this washer to rotate under the wire body, as a result of which it may become awkward to reorient the same.

With certain of Applicant's "sled" and buttress-type implants, it may be necessary to drill two or three holes, and it is thus important that the surgeon not shift the position of the washer as holes are serially drilled.

Further, fixation of the implant is dependent upon the amount of clamping force between the washer and the bone. It may not be possible to consistently develop an optimal clamping force in all applications. For example, in the case of small wire forms, if any resorption occurs under the washer, the clamping force may be diminished. Further, in some cases, the bone is osteoporotic and sufficient force may not be generated due to stripping of the thread in the bone.

In certain applications, the region of the stable bone where the implant is fixed is not flat underlying the region where the washer overlies the wire form. As a result, the washer may not compress against the bone on opposite sides of the implant, whereby inadequate fixation may result. This condition is encountered, for example, with the Applicant's "olecranon sled" implant.

Applicant has developed washers that can be snapped onto a wire form, thereby with the objective of avoiding the difficulty in the handling and applying of separate washers during a surgical procedure. The precision required to allow positive maintenance of the washer on different wire forms makes the commercial production of this type of implant challenging. Even slight deviations from dimensional tolerances could compromise fixation of the implant. Further, this design may not solve the problem associated with forcibly sandwiching the wire form between the washer and bone.

Still further, a captive washer arrangement stacks component thicknesses which could result in patient discomfort, with potential tissue irritation and even damage.

The challenge to continue to improve this basic implant design continues to exist in the medical industry to better address one or more of the above areas.

SUMMARY OF THE INVENTION

In one form, the invention is directed to a method of maintaining a position of a first bone part relative to a second bone part. The method includes the steps of: a) obtaining an apparatus with a unitary body made up of: i) at least one elongate formed wire component with a length; and ii) a base; b) placing the apparatus in an operative position wherein at least a portion of the one elongate formed wire component engages the first bone part; and c) with the apparatus in the operative position, anchoring the base to the second bone part to thereby fix the apparatus in the operative position. The one elongate formed wire component has a first length portion coextensive with, against, and fixed relative to, a portion of the base.

In one form, the base consists of a plate with a peripheral edge. The first length portion is coextensive with a portion of the peripheral edge, against the portion of the peripheral edge, and fixed relative to the portion of the peripheral edge.

In one form, the plate has a thickness at the portion of the peripheral edge. The first length portion has an effective diameter that is greater than or equal to the thickness of the plate at the portion of the peripheral edge.

In one form, a second length portion of the one elongate formed wire component extends from the first length portion to a free end. The one elongate formed wire component has a substantially uniform diameter over the first and second length portions.

In one form, the first length portion is welded to the base.

In one form, the one elongate formed wire component is formed into a "U" shape.

In one form, the at least one elongate formed wire component is formed into a "U" shape with spaced first and second legs. At least a part of the base resides between the spaced first and second legs and is fixed to each of the first and second legs.

In one form, the step of anchoring the base involves directing a fastener through a preformed opening in the base and into the second bone part.

In one form, the at least one elongate formed wire piece defines a U-shaped receptacle. The step of placing the apparatus in an operative position involves situating the apparatus so that at least a part of the first bone part resides in the U-shaped receptacle.

In one form, the step of anchoring the base involves directing a fastener through the base and into the second bone part. The method further includes the step of causing the U-shaped receptacle to be drawn against the at least part of the first bone part so as to thereby urge the first bone part towards the second bone part as an incident of extending the fastener into the second bone part.

In one form, the step of anchoring the base involves anchoring the base using a fastener that is advanced into the second bone part to thereby draw the base towards the second bone part and thereby bear a length of the at least one elongate formed wire component against the second bone part.

In one form, the "U" shape has a base portion from which the first and second legs project and the base is spaced from the base portion.

In one form, the "U" shape has a base portion from which the first and second legs project. The base is located against the base portion.

In one form, the base is a single piece that is fixed to the at least one elongate formed wire component.

In one form, the base consists of first and second pieces each fixed to the at least one elongate formed wire component. The step of anchoring the base involves extending a fastener through each of the first and second pieces and into the second bone part.

In one form, the first bone part is a bone fragment.

In one form, the step of placing the apparatus in an operative position involves directing the at least portion of the one elongate formed wire component into the first bone part.

In one form, the step of placing the apparatus in an operative position involves directing the at least portion of the one elongate formed wire component into the second bone.

In one form, the at least one elongate formed wire component has first and second legs respectively with first and second length portions that coextend in spaced relationship and terminate respectively at first and second free ends.

In one form, the at least one elongate formed wire component has a U-shaped portion with spaced legs. One of the spaced legs is connected to the base and the other of the spaced legs engages the first bone part.

In one form, the base has the form of a substantially flat plate.

In one form, the invention is directed to a method of maintaining a position of a first bone part relative to a second bone part. The method includes the steps of: a) obtaining an apparatus with a unitary body made up of: i) at least one elongate formed wire component with a length and defining first and second wire portions respectively with first and second lengths that are coextensive in spaced relationship; and ii) a base fixedly connected to the first and second lengths; b) placing the apparatus in an operative position wherein at least a portion of the at least one elongate formed wire component engages the first bone part; and c) with the apparatus in the operative position, anchoring the base to the second bone part to thereby fix the apparatus in the operative position.

In one form, the at least one elongate formed wire component is a single piece that defines the first and second legs.

In one form, the one elongate formed wire component has a first length portion coextensive with, against, and fixed relative to, a portion of the base.

In one form, a second length portion of the one elongate formed wire component extends from the first length portion to a free end. The one elongate formed wire component has a substantially uniform diameter over the first and second length portions.

In one form, the at least one elongate formed wire component is formed into a "U" shape with spaced first and second legs. At least a part of the base resides between the spaced first and second legs and is fixed to each of the first and second legs.

In one form, the step of anchoring the base involves anchoring the base using a fastener that is advanced into the second bone part to thereby draw the base towards the second bone part.

In one form, the invention is directed to a method of maintaining a position of a first bone part relative to a second bone part. The method includes the steps of: a) obtaining an apparatus with a unitary body made up of at least one elongate formed wire component and a base that is formed separately from the at least one elongate formed wire component and fixedly joined to the at least one elongate formed wire component; b) placing the apparatus in an operative position wherein at least a portion of the at least one elongate formed wire component on the unitary body engages the first bone part; and c) with the apparatus in the operative position, fixing the base to the second bone part to thereby fix the apparatus in the operative position.

In one form, the invention is directed to an apparatus for maintaining a position of a first bone part relative to a second bone part. The apparatus has a unitary body. The unitary body includes: i) at least one elongate formed wire component with a length; and ii) a base. The one elongate formed wire component has a first length portion coextensive with, against, and fixed relative to, a portion of the base. The apparatus is configured: a) to be placed in an operative position wherein at least a portion of the one elongate formed wire component can engage a first bone part; and b) so that upon a fastener being used to fix the base to a second bone part the apparatus can be maintained in the operative position wherein associated first and second bone parts are maintained in a desired relationship.

In one form, the base and at least one elongate formed wire component are made from at least one medical grade material.

In one form, the apparatus is provided in combination with at least one fastener that is configured to fix the base to bone.

In one form, the at least one fastener is one of: a) a threaded component; b) a peg; and c) a staple.

In one form, the first length portion is welded to the base.

In one form, the base has a peripheral edge. The first length portion is welded to the portion of the base at the peripheral edge.

In one form, the first length portion is welded to the base at first and second discrete locations spaced from each other lengthwise of the one elongate formed wire component.

In one form, the base has a first plate that defines the portion of the base with a bottom surface to face a bone portion to which the base is to be fixed. The first length portion extends to below the bottom surface.

In one form, the base has a first plate with a thickness. The first length portion has an effective diameter that is greater than or equal to the thickness of the first plate.

In one form, a second length portion of the one elongate formed wire component extends from the first length portion to a free end. The one elongate formed wire component has a substantially uniform diameter over the first and second length portions.

In one form, the at least one elongate formed wire component is formed into a "U" shape with spaced first and second legs. At least a part of the base resides between the spaced first and second legs and is fixed to each of the first and second legs.

In one form, the at least one elongate formed wire piece defines a "U" shape with spaced legs. One of the spaced legs is fixed to the base and the other of the spaced legs extends to a free end.

In one form, the at least one elongate formed wire piece has a U-shaped receptacle into which the base extends. The U-shaped receptacle is defined by first and second legs. The base has a first piece that is fixed to each of the first and second legs.

In one form, the base has a second piece spaced from the first piece and fixed to each of the first and second legs.

In one form, the at least one elongate formed wire component has first and second legs respectively with first and second length portions that coextend in spaced relationship and terminate respectively at first and second free ends.

In one form, the first and second legs each is formed into a "U" shape.

DETAILED DESCRIPTION OF THE PREFERRED EMBODIMENT

Figure 1:
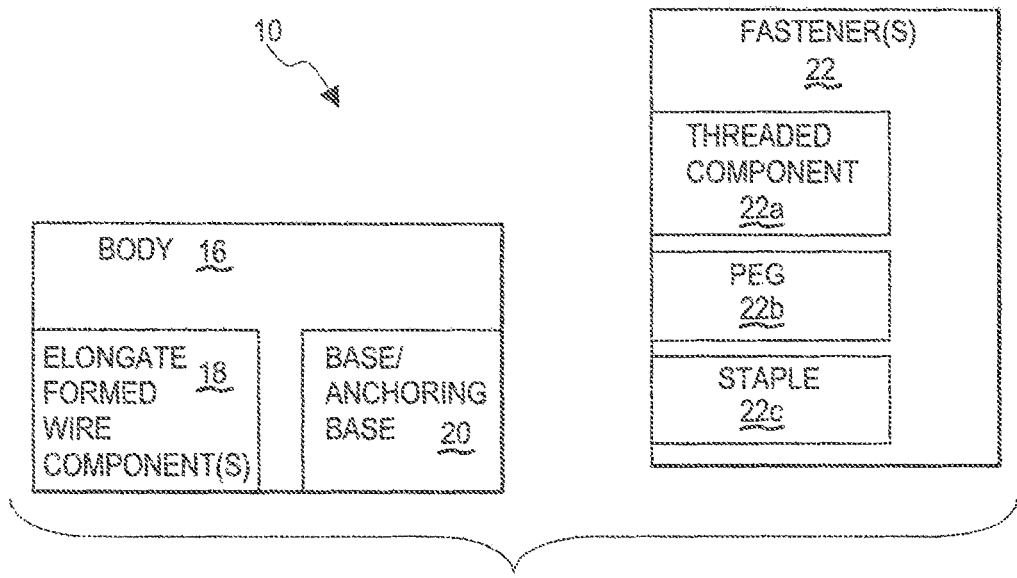
FIG. 1 is a schematic representation of an apparatus for maintaining a position of a first bone part in relationship to a second bone part, according to the invention.
Figure 2:
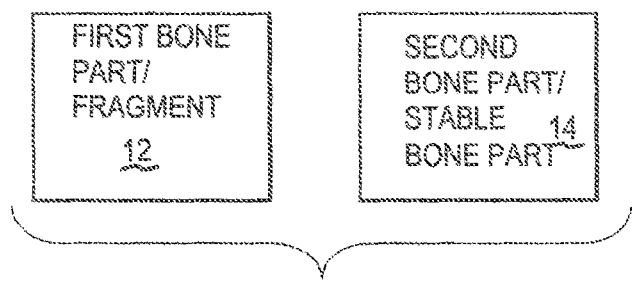
FIG. 2 is a schematic representation of exemplary first and second bone parts identified respectively as a bone fragment and a stable bone part.

In FIG. 1, an apparatus in the category to which the present invention is directed is shown schematically at 10. The apparatus 10 defines an implant that is usable to maintain the position of a first bone part/fragment 12, as shown in FIG. 2, in relationship to a second bone part/stable bone part 14. The apparatus 10 is of the type that can be used in association with many different bones, as encompassed by the generic showing in FIG. 2.

Exemplary applications for this type of apparatus 10 are disclosed in the Applicant's various patents listed in the "Background Art" section, above. The disclosure in each of these patents is incorporated herein by reference. It should be understood that the different applications described therein are not to be viewed as limiting, as the invention can be practiced with virtually any bone parts, regardless of their nature or number, which are to be maintained in a desired relationship.

The apparatus 10 in FIG. 1 consists of a unitary body 16 made up of at least one elongate formed wire component 18 and a base/anchoring base 20 that may be made up of a single piece or multiple pieces.

As used throughout the description herein, a "unitary body" is a body made up of a single piece or multiple pieces that are permanently secured together in a fixed relationship to function as one piece.

The base 20 is configured to directly or indirectly cooperate with at least one fastener 22 that can be used to maintain the apparatus 10 in an operative position relative to the bone parts 12, 14. The generic showing of the fastener 22 is intended to encompass any fastener that cooperates between the base 20 and the second bone part 14 to thereby fix the base 20 to the second bone part 14.

Within the generic showing in FIG. 1 are an exemplary threaded component/screw 22a, a peg 22b, and a staple 22c. These examples are not all-inclusive of the fasteners contemplated. Within the generic showing of the fastener 22 is also any structure that might clamp the base 20 in place relative to the second bone part 14.

The formed wire component is configured to engage at least the first bone part 12, and potentially the second bone part 14, with the apparatus 10 in an operative position, which operative position is maintained by using one or more appropriate fasteners 22 to fix the base 20 to the second bone part 14.

Figure 3:
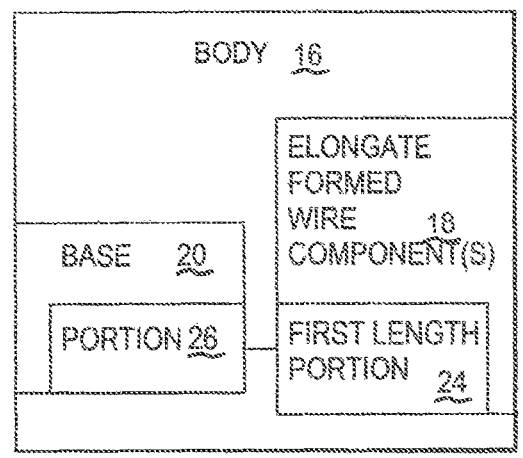
FIG. 3 is a schematic representation showing further details of a unitary body on the inventive apparatus in FIG. 1.

In FIG. 3, one exemplary form of unitary body 16 is shown in further detail. The elongate formed wire component 18 has a first length portion 24 that is coextensive with, placed against, and fixed relative to a portion 26 of the base 20. The portion 26 may be any part of the base 20 and in one exemplary form is on a peripheral edge of the base 20.

As noted above, the bone part 12 may be a bone fragment formed by a fracture of the bone defining the second bone part 14. The generic showing is also intended to encompass any apparatus 10 that serves as a foundation for a bone fragment 12 that is at least partially constructed, as by a grafting process.

As noted above, the generic showing of the elongate formed wire component 18 is not limited to any particular shape or diameter. Further, while a single wire is shown in each apparatus herein, multiple wire pieces could be utilized to produce the same or similar shapes. The generic showing is intended to encompass any elongate component that is of uniform or varying diameter that is strategically shaped and placed to facilitate retention of the first bone part 12 relative to the second bone part 14, be it by defining a receptacle for the first bone part 12, bearing against a surface of the first bone part, and/or by penetration thereof.

Without limitation, exemplary forms of the elongate formed wire component 18 are shown in the aforementioned patents, incorporated herein by reference.

As noted above, the elongate formed wire component 18 may have a substantially constant diameter or may vary in diameter. Commonly, the cross-sectional shape will be substantially circular, however this is not required. As one example, the diameter may be on the order of 0.045 to 0.090 inches. The diameter of the elongate formed wire component 18 may be slightly greater where there is connection to the base 20 to add greater stability and reduce elasticity, while having a stepped or tapered diameter therefrom. Alternatively, a smaller diameter at the base connection may facilitate formation and result in a more compact design. Regions that are bent may have a locally reduced diameter to facilitate formation. The formed portions extending away from the base 20 may have a larger diameter to exhibit the necessary strength and resistance to bending while potentially being semi-elastic in nature to allow some adaptation to conditions at different surgical sites.

Similarly, the generically depicted base 20 is not limited in terms of its construction. As noted, the base 20 may be made up of one or more parts that can be suitably fixed relative to the second bone part 14. Each base part may be made substantially flat or may be contoured to conform to the patient's anatomy at the operating site. The plate shapes may have a uniform thickness or varying thickness.

For purposes of simplicity, the exemplary bases described herein will be shown fixed relative to the second bone part by a fastener that extends through the base 20 to purchase bone thereunder or thereadjacent. As noted, this construction is not required.

Typically, the elongate formed wire component(s) 18 and base 20 will be made from a medical grade material. In the event that the unitary body 16 is made from separate parts that are united, such process typically will be accomplished by welding. With metal components, typically a laser welding process is utilized.

Further, permanent connection may also be accomplished through a permanent bonding process, including, but not limited to, one utilizing adhesives or fused materials. As one example, plastic material may be ultrasonically bonded to the metal of the formed wire component 18. Further, interdigitation of one material to another, such as, but not limited to, a porous surface on another, etc. might be practiced.

The invention also contemplates formation of the unitary body from a single piece of material.

Exemplary forms of the invention will now be described.

Figure 4:
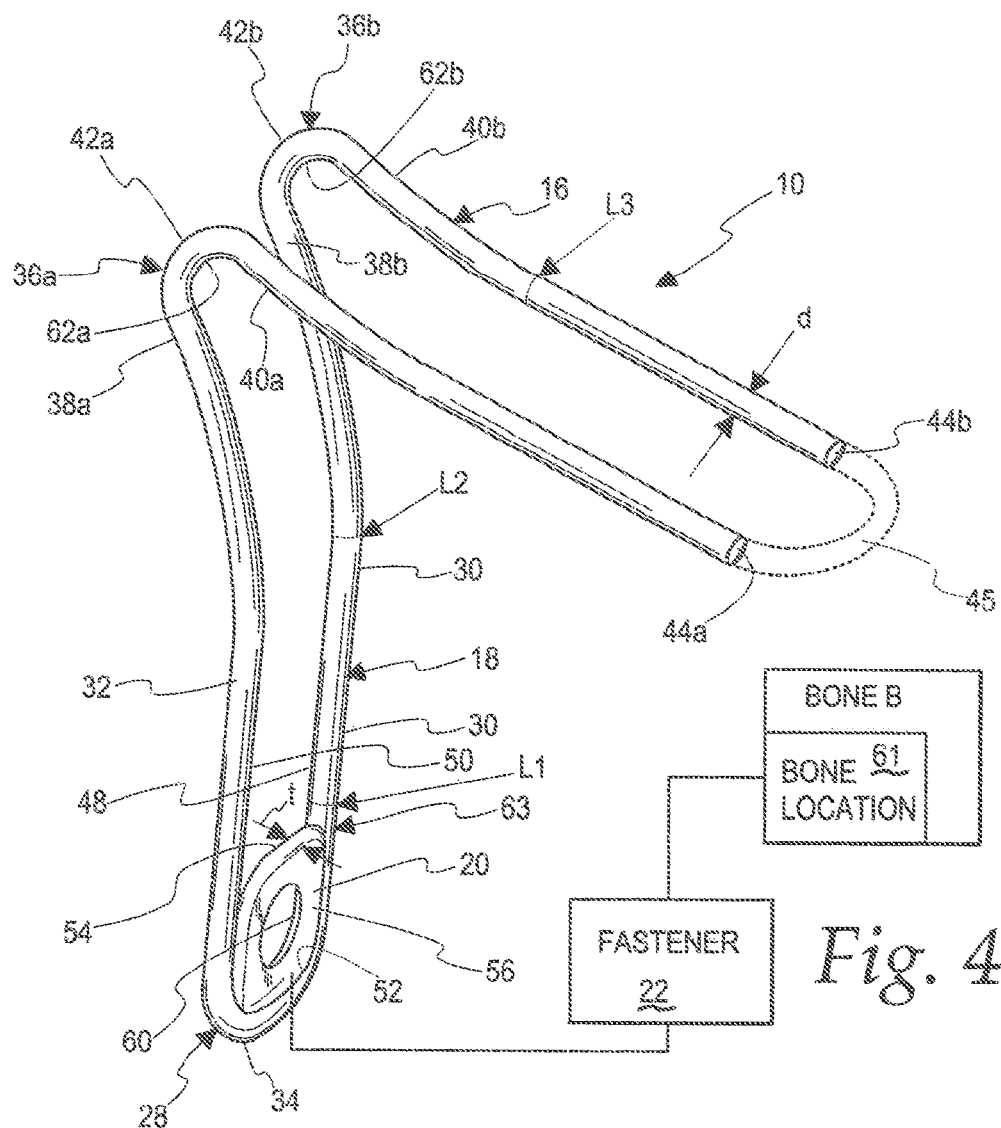
FIG. 4 is a bottom perspective view of one specific form of the inventive apparatus, as shown schematically in FIG. 1.
Figure 5:
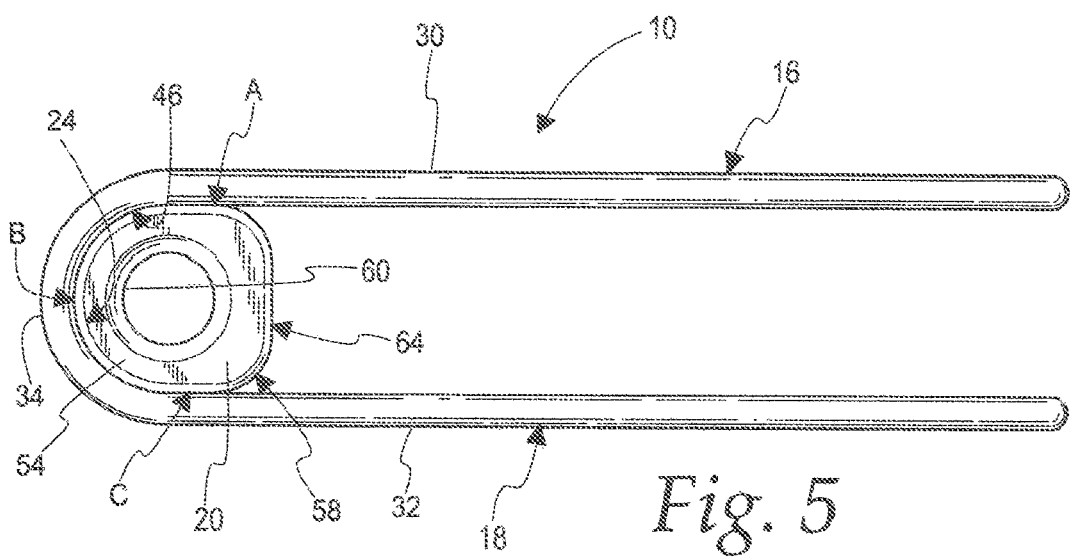
FIG. 5 is a plan view of the apparatus in FIG. 4.

In FIGS. 4 and 5, one exemplary form of the apparatus 10 is shown that incorporates a buttressing capability. In this embodiment, the body 16 consists of a single, elongate formed wire component 18. The elongate formed wire component 18 has a U-shaped mounting portion 28 defined by legs 30, 32 projecting in spaced relationship away from a base/base portion 34.

The leg 32 extends to define a separate U-shaped portion 36a with spaced legs 38a, 40a projecting away from a base 42a. The leg 30 extends into a like form, including a U-shaped portion 36b with legs 38b, 40b projecting away from a base 42b.

The legs 40a, 40b coextend in spaced relationship from respective bases 42a, 42b to unconnected free ends 44a, 44b. The free ends 44a, 44b in this buttressing configuration, and corresponding free ends in other embodiments herein, may be connected by making the legs 40a, 40b contiguous with each other or by using a separate element 45, as shown in dotted lines in FIG. 4. For purposes of simplicity the leg ends 44a, 44b will be considered "free ends", whether or not connected to each other.

In this embodiment, the base 20 is in the form of a flat plate and nests conformingly within a U-shaped receptacle 46 defined on the U-shaped mounting portion 28 by facing leg edges/surfaces 48, 50, respectively on the legs 30, 32, and an edge/surface 52 on the base 34 connecting between the edges/surfaces 48, 50.

The base/plate 20 has oppositely facing surfaces 54, 56 that in this embodiment are substantially parallel so that the base/plate has a substantially uniform thickness t. As noted, contoured surfaces may be utilized to conform to an underlying bone.

By conforming a peripheral edge 58 on the base/plate 20 to the edges/surfaces 48, 50, 52, a solid foundation is defined that affords a region of potentially high strength and rigidity.

The portion of the elongate formed wire component 18 that is coextensive with, against, and fixed relative to the peripheral edge 58 corresponds to the first length portion 24, as identified schematically in FIG. 3.

The first length portion 24 may be unitarily joined with the peripheral edge 58 over its entire length, as by welding, adhesive, etc. Welding is preferred to establish a permanent positive connection.

Alternatively, the first length portion 24 can be fixed to the peripheral edge 58 at discrete, spaced locations, with representative locations being identified at A, B, and/or C. In this case a weld is made between the base 20 and each of the legs 30, 32 and base 34.

Once the unitary body 16 is defined, it can be fixed in its operative position. To accomplish this, the base 20 is provided with a single, fully surrounded opening 60 through which a fastener 22 can be extended into a bone or bones, generically identified at B, at a bone location 61.

With this configuration, typically the legs 40a, 40b will be directed into the first bone part 12. Alternatively, or in addition to this penetration, the U-shaped portions 36a, 36b respectively define receptacles 62a, 62b that individually or cooperatively engage the first bone part 12 which has at least a part that is at least nominally matched to the shape thereof to allow a captive arrangement to be established.

In this embodiment, the apparatus can perform both a captive function and a buttressing function, depending upon the particular bone and the condition thereof.

As depicted, the diameter of the elongate formed wire component 18, identified as d, is substantially uniform along its entire length. Alternatively, different diameters might be strategically selected as to facilitate formation and/or provide controlled rigidity at different parts of the apparatus 10. A typical diameter for the elongate formed wire component 18 is in the range of 0.045 inches to 0.090 inches. This diameter is not limiting, as it is contemplated that the diameter could be substantially greater than 0.090 inches or less than 0.045 inches.

The relationship of the "bottom" surface, that directly overlies the bone, and the bone at the anchoring location is not limited. The elongate formed wire component 18 and base/plate 20 may be joined in different manners and may have different shapes and dimensional relationships depending upon the particular application.

In one form, the bottom plate surface 56 is flush with the bottom edge 63 defined by the U-shaped mounting portion 28 so that the surface 56 and edge 63 seat simultaneously against a complementarily-shaped bone surface. The plate surface 56 may extend to below the bottom edge 63 to be the primary bone contacting surface in the vicinity of the fastener 22.

Alternatively, the surface 56 can be slightly above the edge 63, whereby drawing of the base/plate 20 towards the bone location 61 bears at least part of the edge 63 positively against the bone before the surface 56 makes engagement. Alternatively, the surface 56 may be maintained above the bone B at the location 61.

In one preferred form, the thickness t of the base/plate 20 is less than the diameter d for the elongate formed wire component 18, whereby the base/plate surfaces 54, 56 can reside within the diameter d of the elongate formed wire component 18. As noted, the diameter d may be greater than or equal to the thickness t.

With the surface 56 spaced slightly from the bone at the location 61, a residual biasing force may be imparted to the base/plate 20 through a securing fastener 22, which may contribute to a more positive connection.

A slight downward recess of the base/plate surface 54 from the top edge of the U-shaped mounting portion 28 defined by the elongate formed wire component 18 may avoid localized projection that could irritate overlying tissue.

As depicted, the legs 40a, 40b coextend in spaced relationship and terminate at the free ends 44a, 44b, respectively. However, this coextension is not required and potentially part or all of one of the legs 40a, 40b might be changed in shape or length in relationship to the other, or altogether eliminated. As shown in FIG. 4, the apparatus 10 might be changed by eliminating part of the leg 30, as shown in dotted lines at alternative locations L2, L3, or all or substantially all of the leg 30 as shown in dotted lines at L3. These are just examples of virtually an unlimited number of different variations that might be made. Further, the matching shape, and substantially parallel relationship over the coextension of the legs 30, 32 is not required.

The legs 32, 40a and legs 30, 40b can also be considered to be each separately making up the U-shaped portions 36a, 36b, with the legs 32, 30 fixed to the base/plate 20 and the legs 40a, 40b extending to the free ends 44a, 44b, respectively.

As noted above, the elongate formed wire component 18 may have a uniform diameter d. Alternatively, different length portions may have different diameters. For example, the length portions defined by the legs 40a, 40b may have a diameter different than the first length portion 24, or the same diameter. The former construction potentially facilitates bending of the U-shaped portion connected to the base/plate 20 while allowing portions other than the first length portion 24 to be more rigid for greater integrity and resistance to bending.

As shown in the drawings, as with all embodiments herein, all exposed edge regions 64 on the base/plate 20 are rounded to avoid tissue irritation.

Figure 6:
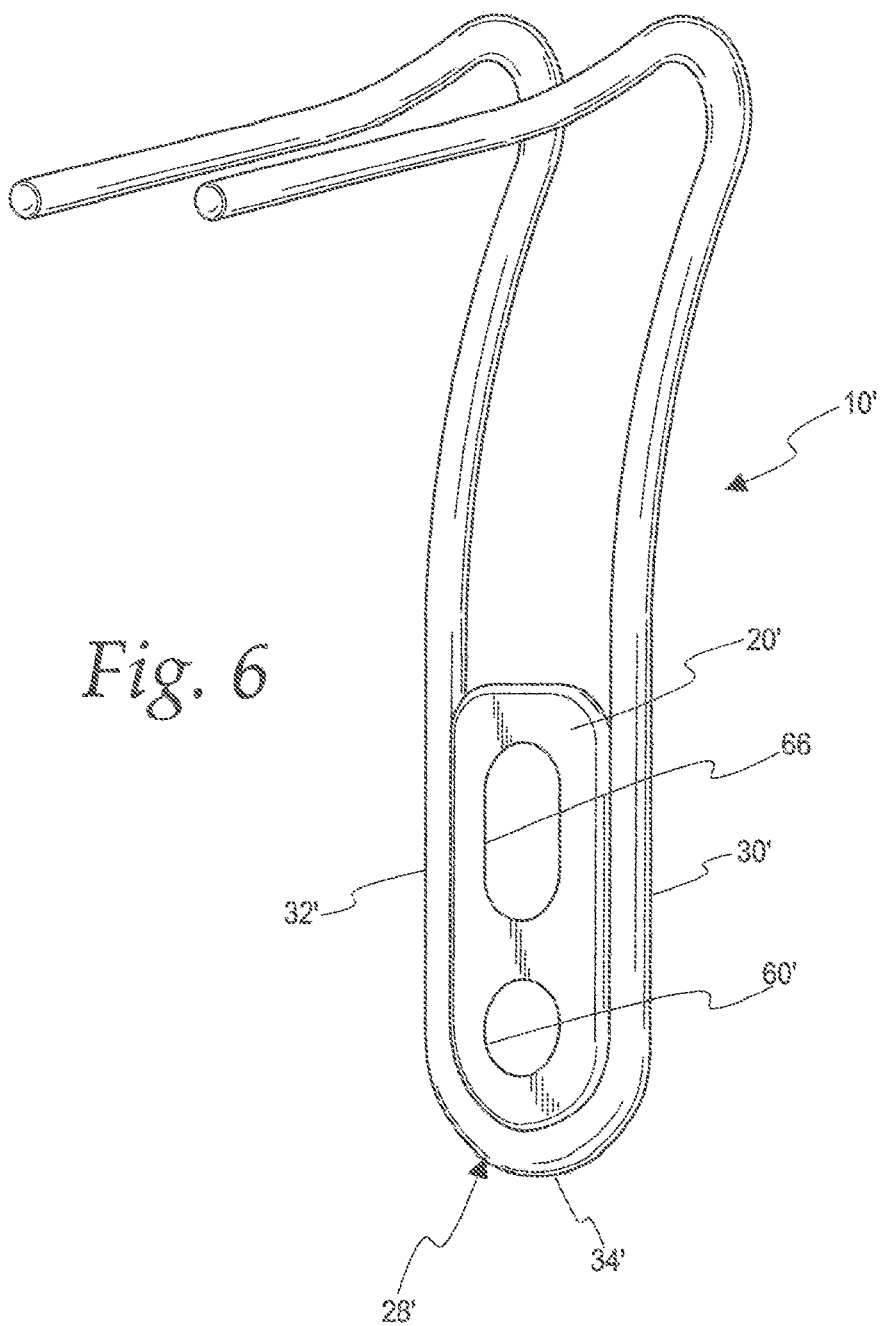
FIG. 6 is a bottom perspective view of a further modified form of the inventive apparatus, as shown in FIG. 1.
Figure 7:
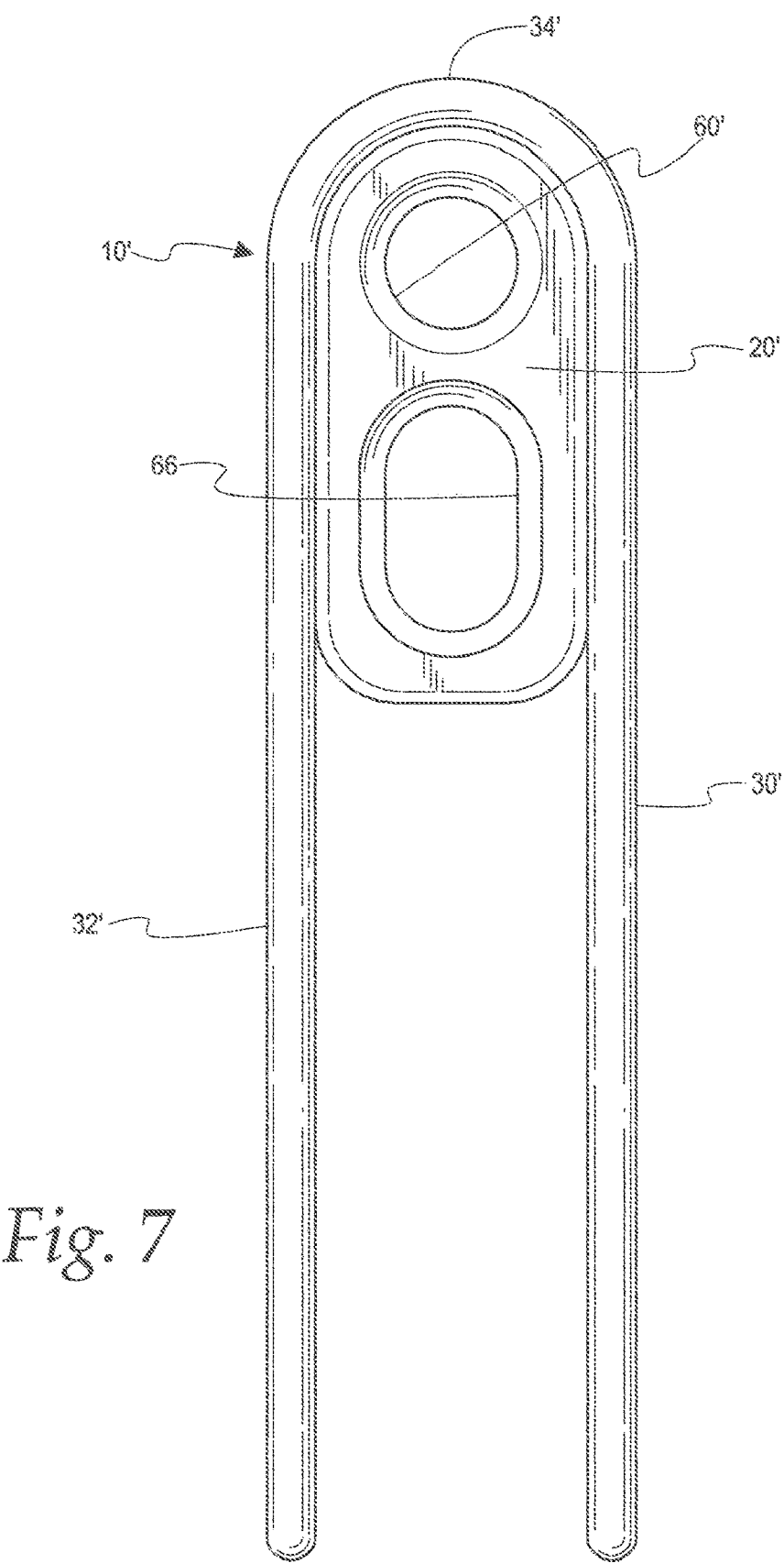
FIG. 7 is a plan view of the apparatus in FIG. 6.

In FIGS. 6 and 7, a modified form of the apparatus is shown at 10', which apparatus is substantially the same as the apparatus 10, with the primary distinction being that the corresponding base 20' extends away from the base 34' of the U-shaped mounting portion 28' further along the length of the legs 30', 32'. The extended base configuration provides an increased area to form an elongate/oval opening 66, in addition to the opening 60'. The opening 66 accepts a corresponding fastener 22 and allows a fastener 22 to be directed therein at different locations. This permits more strategic placement of a fastener and/or allows guided relative movement to occur between the apparatus 10' and the bone, as before a separate fastener 22 is directed through the opening 60' to fix a precise position.

As depicted, both of the openings 60', 66 are fully surrounded by the plate/base 20'.

Figure 8:
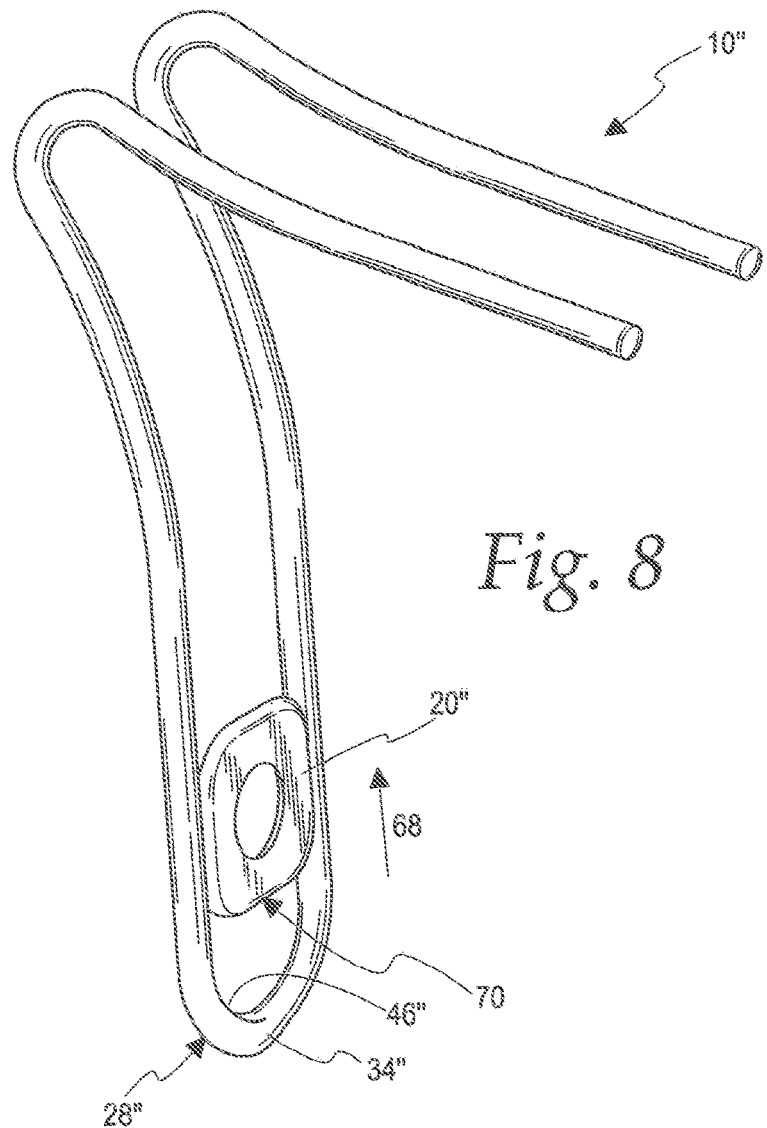
FIG. 8 is a bottom perspective view of a further modified form of the inventive apparatus, as shown in FIG. 1.

In FIG. 8, a further modified form of apparatus is shown at 10" that differs from the apparatus 10 principally by reason of the base/plate 20" being shifted in the direction of the arrow 68 away from the base 34" of the U-shaped portion 28".

The peripheral edge portion at 70 also is slightly different in that it does not have to have a shape conforming to that of the receptacle 46" defined by the U-shaped portion 28".

Figure 9:
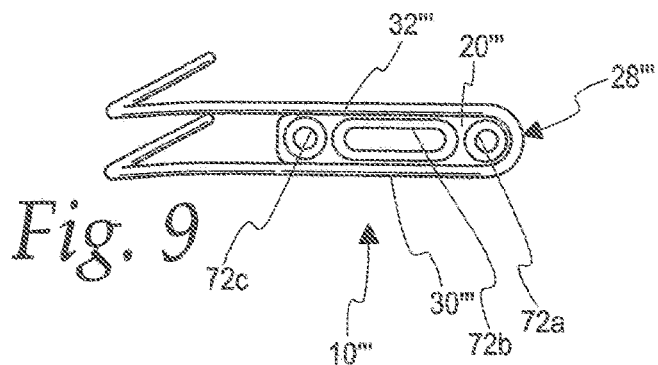
FIG. 9 is a top, perspective view of still another form of the inventive apparatus, as shown in FIG. 1.

In FIG. 9, a further modified form of apparatus is shown at 10''' that is similar to the apparatus 10', with the primary distinction being that the base/plate 20''' is longer in a direction parallel to the length of the legs 30''', 32" on the U-shaped portion 28" and has three separate fastener openings 72a, 72b, 72c, each fully surrounded by the base/plate 20'''.

The opening 72a corresponds to the opening 60' with substantially the same configuration and location. The elongate/oval opening 72b corresponds to the opening 66 with its major axis extended further along the length of the legs 30''', 32''. A second circular opening 72c is provided, with the elongate opening 72b located between the circular openings 72a, 72c.

Figure 10:
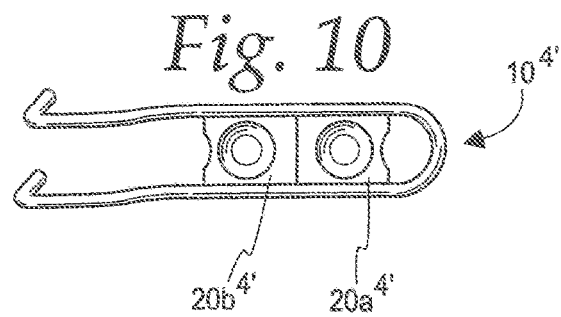
FIG. 10 is a top, perspective view of a further modified form of the inventive apparatus, as shown in FIG. 1.

In FIG. 10, a further form of apparatus is shown at $10^{4'}$, with a base made up of separate, but like, plates/pieces $20a^{4'}$, $20b^{4'}$ with the piece $20a^{4'}$ corresponding generally to the base/plate 20'' in FIG. 8. The base piece $20b^{4'}$ may abut to the base piece $20a^{4'}$ or may be spaced therefrom.

Figure 11:
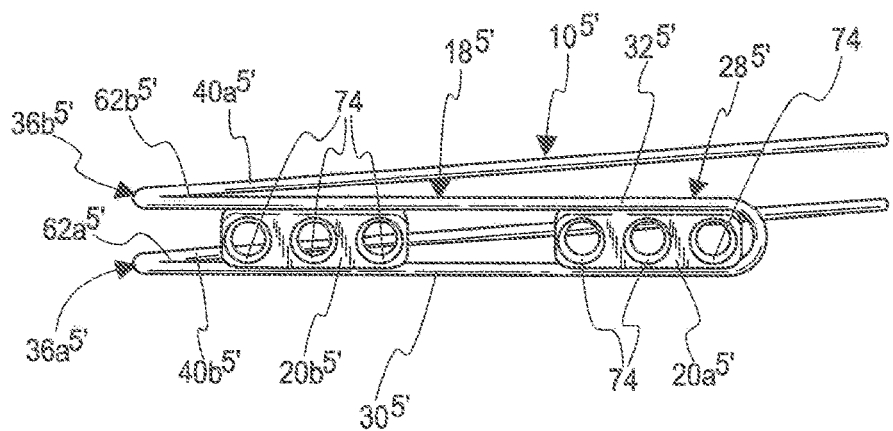
FIG. 11 is a top, perspective view of a still further modified form of the inventive apparatus, as shown in FIG. 1.

In FIG. 11, a further modified form of apparatus is shown at $10^{5'}$ with a configuration performing the function of the aforementioned "sled" device, described above. In this embodiment, a single elongate formed wire component $18^{5'}$ defines a U-shaped mounting portion $28^{5'}$ with separate base pieces $20a^{5'}$, $20b^{5'}$, spaced lengthwise of, and spanning between, the legs $30^{5'}$, $32^{5'}$ on the U-shaped portion $28^{5'}$. Each base piece $20a^{5'}$, $20b^{5'}$ is preferably fixed to both legs $30^{5'}$, $32^{5'}$. Each of the parts $30^{5'}$, $32^{5'}$ has three like openings 74 for suitable fasteners 22 that may be extended therethrough into bone at any one or more opening locations.

The "sled" apparatus configuration differs from the aforementioned buttress configurations primarily by reason of corresponding legs $40a^{5'}$, $40b^{5'}$ projecting at a smaller angle to the legs $30^{5'}$, $32^{5'}$ at the U-shaped portions $36a^{5'}$, $36b^{5'}$ so as to produce receptacles $62a^{5'}$, $62b^{5'}$ typically used to accommodate one or more bone fragments, to thereby captively maintain the bone fragments against a stabilizing bone part to which the U-shaped portion $28^{5'}$ is fixed through the base pieces $20a^{5'}$, $20b^{5'}$. In addition, the legs $40a^{5'}$, $40b^{5'}$ engage the first bone part 12 as well as the second bone part 14.

In FIGS. 12-17, a further modified form of apparatus is shown at $10^{6'}$ in a form Assignee identifies as its "Olecranon Sled" implant, shown operatively positioned with respect to a first bone part 12 and second bone part 14.

The apparatus has a unitary body $16^{6'}$ with an elongate formed wire component $18^{6'}$ fixed to a base $20^{6'}$ as in prior embodiments.

A U-shaped mounting portion $28^{6'}$ has spaced legs $30^{6'}$, $32^{6'}$ which project in spaced relationship away from the base $20^{6'}$. The legs $30^{6'}$, $32^{6'}$ extend into U-shaped portions $36b^{6'}$, $36a^{6'}$, respectively having legs $40a^{6'}$, $40b^{6'}$. The U-shaped portions $36a^{6'}$, $36b^{6'}$ respectively define receptacles $62b^{6}$, $62a^{6'}$.

The legs $40a^{6'}$, $40b^{6'}$ extend through the first bone part 12 and into the second bone part 14, whereby a part of the first bone part 12 resides within the receptacles $62a^{6'}$, $62b^{6'}$. The base $20^{6'}$ overlies the second bone part 14 at a location spaced from a fracture site at F.

In this embodiment, the base $20^{6'}$ has similarly configured openings $80a^{6'}$, $80b^{6'}$. Exemplary opening $80a^{6'}$ has an elongate shape with a beveled edge $82a^{6'}$ which surrounds the opening $80a^{6'}$ at all but the edge region $84a^{6'}$ at one lengthwise end of the opening $80a^{6'}$.

An exemplary fastener $22^{6'}$ has a head 86 with a tapered region 88 extending to a threaded shank 90.

Figure 16:
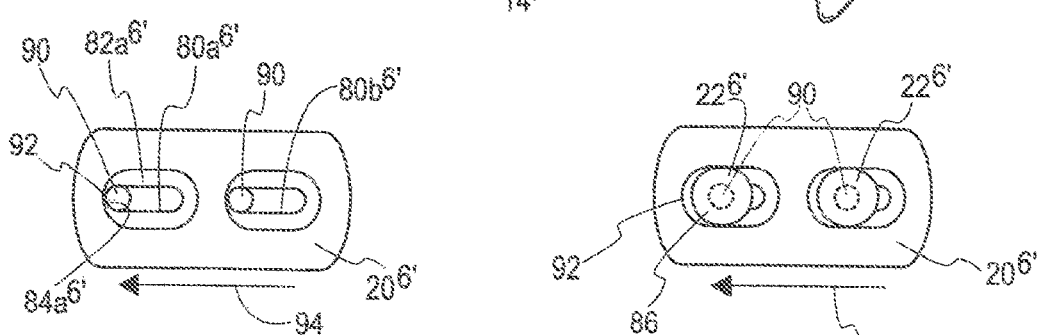
FIG. 16 is an enlarged, plan view of a base on the apparatus in FIGS. 12-15 with fasteners initially being directed into openings on the base and heads of the fasteners removed.
Figure 17:
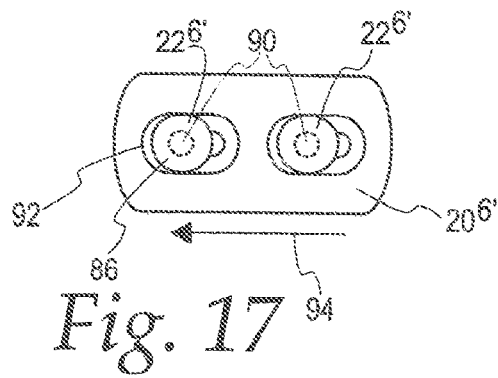
FIG. 17 is a view as in FIG. 16 wherein the fasteners are tightened so as to cause the base to shift relative to the fasteners.

With the apparatus $10^{6'}$ operatively positioned, the shank 90 can be directed through the opening $80a^{6'}$ adjacent to the region $84a^{6'}$, as seen in FIG. 16. As the fastener $22^{6'}$ is advanced, the tapered region 88 encounters an edge 92 at the region $84a^{6'}$, whereupon a camming action occurs that wedges the base $20^{6'}$ in the direction of the arrow 94. As this occurs, the U-shaped portions $36a^{6'}$, $36b^{6'}$ draw the first bone part 12 towards the second bone part 14. Ultimately, the fastener $22^{6'}$ assumes the FIG. 17 position with the fastener $22^{6'}$ fully tightened. The same type of fastener $22^{6'}$ can be used in the opening $80b^{6'}$.

Alternatively, only one of the openings $80a^{6'}$, $80b^{6'}$ may be required to allow the camming action.

Further details of the construction and intended use of the sled and buttress-type apparatus are provided in the Applicant's previously issued patents, identified above, and incorporated herein by reference.

Figure 18:
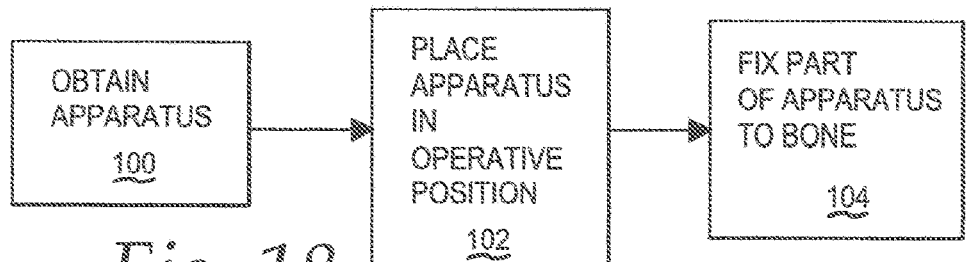
FIG. 18 is a flow diagram representation of a method of maintaining a first bone part in relationship to a second bone part, according to the invention.
Figure 12:
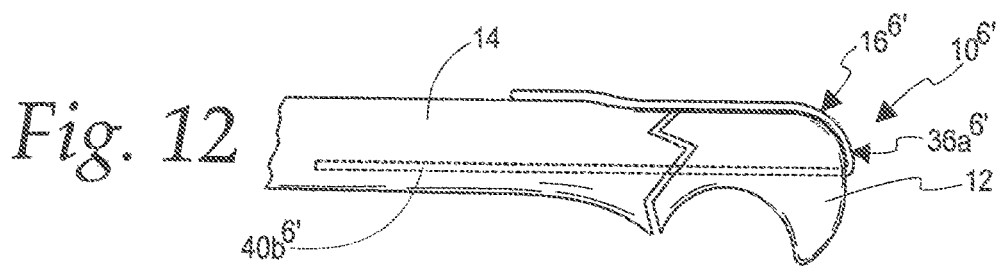
FIG. 12 is a side elevation view of first and second bone parts produced by a fracture at the olecranal region of a patient and with another form of the inventive apparatus in an operative position.
Figure 13:
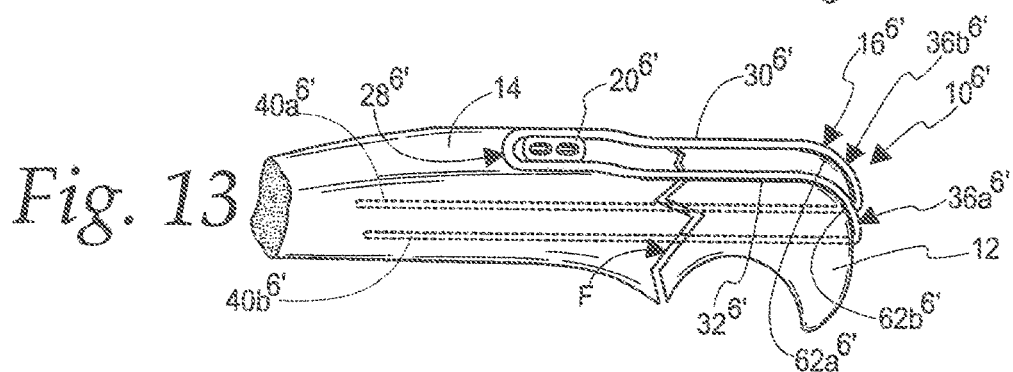
FIG. 13 is a perspective view of the components in FIG. 12.
Figure 14:
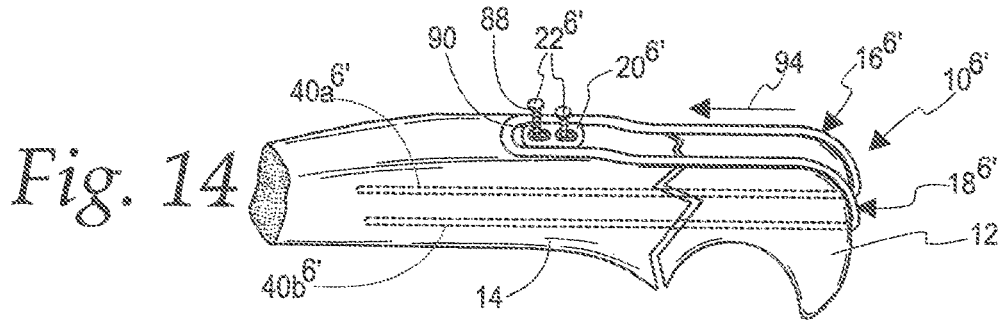
FIG. 14 is a view as in FIG. 13 wherein fasteners are being directed into a base on the apparatus.
Figure 15:
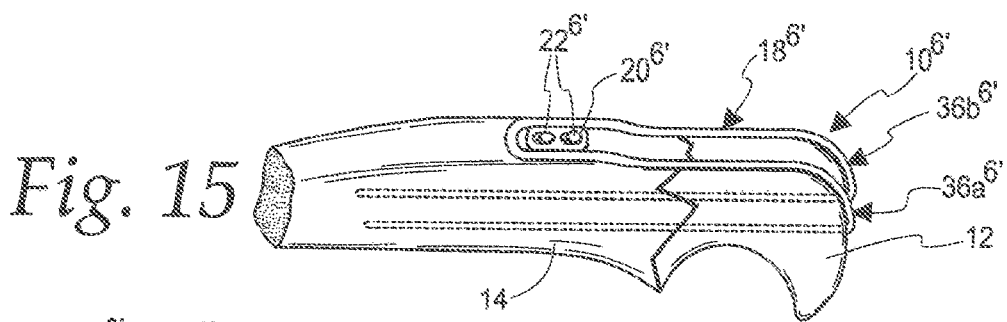
FIG. 15 is a view as in FIG. 14 wherein the fasteners are fully tightened as an incident of which the first bone part is drawn towards the second bone part.

As shown in flow diagram form in FIG. 18, using the above apparatus, a method of maintaining a position of a first bone part in relationship to a second bone part can be performed as follows.

As shown at block 100, an apparatus as described above is obtained including a unitary body made up of at least one elongate formed wire component and at least part of a base.

As shown at block 102, the apparatus is placed in an operative position wherein the at least one elongate formed wire component engages the second bone part.

As shown at block 104, with the apparatus in the operative position, a fastener is used to fix the base in relationship to the first bone part.

It is also contemplated that the fastener 22 can be directed into the second bone part as well as the first bone part to maintain a relationship with the apparatus.

As described in the incorporated prior art, various portions of the different apparatus may be directed into the second bone part 14, the first bone part 12, and/or engage externally in a bearing relationship.

The foregoing disclosure of specific embodiments is intended to be illustrative of the broad concepts comprehended by the invention.

The invention claimed is:

1. A method of maintaining a position of a first bone part relative to a second bone part, the method comprising the steps of:
   a) obtaining an apparatus comprising a unitary body,
   the unitary body comprising: i) at least one elongate formed wire component with a length; and ii) a base,
   the at least one elongate formed wire component having a first length portion coextensive with, against, and fixed relative to, a portion of the base;
   b) placing the apparatus in an operative position wherein at least a portion of the at least one elongate formed wire component engages the first bone part; and
   c) with the apparatus in the operative position, anchoring the base to the second Pone part to thereby fix the apparatus in the operative position,
   wherein the at least one elongate formed wire component defines a U-shaped receptacle,
   wherein the step of placing the apparatus in an operative position comprises situating, the apparatus so that at least a part of the first bone part resides in the U-shaped receptacle,
   wherein the base comprises a plate with a peripheral edge and the first length portion is coextensive with a portion of the peripheral edge, against the portion of the peripheral edge, and fixed relative to the portion of the peripheral edge.

2. The method of maintaining a position of a first bone part relative to a second bone part according to claim 1 wherein the plate has a thickness at the portion of the peripheral edge and the first length portion has an effective diameter that is greater than or equal to the thickness of the plate at the portion of the peripheral edge.

3. A method of maintaining a position of a first bone part relative to a second bone part, the method comprising the steps of:

a) obtaining an apparatus comprising a unitary body,
the unitary body comprising: i) at least one elongate formed wire component length; and ii) a base,
the at least one elongate formed wire component having a first length portion coextensive with, against, and fixed relative to, portion of the base;
b) placing the apparatus in an operative position wherein at least a portion one elongate formed wire component engages the first bone part; and
c) with the apparatus the operative position, anchoring the base to the second bone part to thereby fix the apparatus in the operative position,
wherein the at least one elongate formed wire component defines a U-shaped receptacle,
wherein the step of placing the apparatus in an operative position comprises situating the apparatus so that at least a part of the first bone part resides in the U-shaped receptacle,
wherein the first length portion is welded to the base.

4. A method of maintaining a position of a first bone part relative to a second bone part, the method comprising the steps of:
a) obtaining an apparatus comprising a unitary body,
the unitary body comprising: i) at least one elongate formed wire component with a length; and ii) a base,
the at least one elongate formed wire component having a first length portion coextensive with, against, and fixed relative to, a portion of the base;
b) placing the apparatus in an operative position wherein at least a portion of the at least one elongate formed wire component engages the first bone part; and
c) with the apparatus in the operative position, anchoring the base to the second bone part to thereby fix the apparatus in the operative position,
wherein the at least one elongate formed wire component defines a U-shaped receptacle and the step of placing the apparatus in an operative position comprises situating the apparatus so that at least a part of the first bone part resides in the U-shaped receptacle,
wherein the step of anchoring the base comprises extending a fastener through the base and into the second bone part and further comprises the step of causing the U-shaped receptacle to be drawn against the at least a part of the first bone part so as to thereby urge the first bone part towards the second bone part as an incident of extending the fastener into the second bone part.

5. A method of maintaining a position of a first bone part relative to a second bone part, the method comprising the steps of:
a) obtaining an apparatus comprising a unitary body,
the unitary body comprising: i) at least one elongate formed wire component with a length; and ii) a base,
the at least one elongate formed wire component having a first length portion coextensive with, against, and fixed relative to, a portion of the base;
b) placing the apparatus in an operative position wherein at least a portion of the at least one elongate formed wire component engages the first bone part; and,
c) with the apparatus in the operative Position, anchoring the base to the second bone part to thereby fix the apparatus in the operative position,
wherein the at least one elongate formed wire component defines a U-shaped receptacle,
wherein the step of placing the apparatus in an operative position comprises situating the apparatus so that at least a part of the first bone part resides in the U-shaped receptacle,
wherein the step of anchoring the base comprises anchoring the base using a fastener that is advanced into the second bone part to thereby draw the base towards the second bone part and thereby bear a length of the at least one elongate formed wire component against the second bone part.

6. A method of maintaining a position of a first bone part relative to a second bone part, the method comprising the steps of:
a) obtaining an apparatus comprising a unitary body,
the unitary body comprising: i) at least one elongate formed wire component with a length; and ii) a base,
the at least one elongate formed wire component having a first length portion coextensive with, against, and fixed relative to, a portion of the base;
b) placing the apparatus in an operative position wherein at least a portion of the at least one elongate formed wire component engages the first bone part; and
c) with the apparatus in the operative position, anchoring base to the second bone part to thereby fix the apparatus in the operative position,
wherein the at least one elongate formed wire component defines a U-shaped receptacle,
wherein the step of placing the apparatus in an operative position comprises situating the apparatus so that at least a part of the first bone part resides in the U-shaped receptacle,
wherein the base comprises first and second pieces each fixed to the at least one elongate formed wire component and the step of anchoring the base comprises extending a fastener through each of the first and second pieces and into the second bone part.

7. An apparatus for maintaining a position of a first bone part relative to a second bone, the apparatus comprising:
a unitary body,
the unitary body comprising: i) at least one elongate formed wire component with a length; and ii) a base in the form of a first flat plate that is elongate with a length,
the at least one elongate formed wire component having a first length portion coextensive with the length of the first flat plate, against, and fixed relative to, a lengthwise portion of the first flat plate,
the apparatus configured: a) to be place in an, operative position wherein at least a portion of the at least one elongate formed wire component can engage a first bone part and b so that upon a fastener being used to fix the base to a second bone pert the apparatus can be maintained in the operative position; wherein associated first and second bone parts are maintained in a desired relationship,
wherein the first length portion is welded to the first flat plate.

8. The apparatus for maintaining a position of a first bone part relative to a second bone part according to claim 7 wherein the first length portion is welded to the first flat plate at first and second discrete locations spaced from each other lengthwise of the at least one elongate formed wire component.

9. An apparatus for maintaining a position of a first bone part relative to a second bone part, the apparatus is comprising,
a unitary body,
the unitary body comprising: i) at least one elongate formed wire component with a length, and ill a base in the form of a first flat plate that is elongate with a length, the at least one elongate formed wire component having a first length portion coextensive with the length of the first flat plate, against, and fixed relative to, a lengthwise portion of the first flat plate, the apparatus configured: a) to be placed in an operative: position wherein at least a portion of the at least one elongate formed wire component can engage a first bone part; and b) so that upon a fastener being used to fix the base to a second bone part, the apparatus can be maintained in the operative position wherein associated first and second bone parts are maintained in a desired relationship, wherein the first flat plate has a peripheral edge and the first length portion is welded to the portion of the first flat plate at the peripheral edge.

10. An apparatus for maintaining a position of a first bone part relative to a second bone part, the apparatus comprising:

a unitary body, the unitary body comprising: it at least one elongate formed wire component with length; and ii) a base in the form of a first flat plate that is elongate with a length, the at least one elongate formed wire component having a first length portion coextensive with the length of the first flat plate, against, and fixed relative to, a lengthwise portion of the first flat plate, the apparatus configured: a) to be placed in an operative position wherein at least portion of the at least one elongate formed wire component can engage a first bone part; and b) so that upon a fastener being used to fix the base to a second bone part, the apparatus can be maintained in the operative position wherein associated first and second bone parts are maintained in a desired relationship, wherein the first flat plate defines the portion of the base with a bottom surface to face a bone portion to which the base is to be fixed and the first length portion extends to below the bottom surface.

11. An apparatus for maintaining a position of a first bone part relative to a second bone part, the apparatus comprising:

a unitary body, the unitary body comprising: i) at least one elongate formed wire component with a length; and ii) a base in the form of first flat plate that is elongate with a length, the at least one elongate formed wire component having a first length portion coextensive with the length of the first flat plate against, and fixed relative to, a lengthwise portion of the first flat plate, the apparatus configured: a) to be placed in an operative position wherein at least a portion of the at least one elongate formed wire component can engage a first bone part; and bi so that, upon a fastener being used to fix the base to a second bone part, the apparatus can be maintained in the operative position wherein associated first and second bone parts are maintained in a desired relationship, wherein the first flat plate has a thickness and the first length portion has an effective diameter that is greater than or equal to the thickness of the first flat plate.

* * * * *

UNITED STATES PATENT AND TRADEMARK OFFICE
CERTIFICATE OF CORRECTION

PATENT NO. : 11,986,227 B2
APPLICATION NO. : 17/152253
DATED : May 21, 2024
INVENTOR(S) : Robert Medoff It is certified that error appears in the above-identified patent and that said Letters Patent is hereby corrected as shown below:

In the Claims

Claim 1 should read:
1. A method of maintaining a position of a first bone part relative to a second bone part, the method comprising the steps of:
    a) obtaining an apparatus comprising a unitary body,
    the unitary body comprising: i) at least one elongate formed wire component with a length; and
        ii) a base,
    the at least one elongate formed wire component having a first length portion coextensive with, against, and fixed relative to, a portion of the base;
    b) placing the apparatus in an operative position wherein at least a portion of the at least one elongate formed wire component engages the first bone part; and
    c) with the apparatus in the operative position, anchoring the base to the second bone part to thereby fix the apparatus in the operative position,
    wherein the at least one elongate formed wire component defines a U-shaped receptacle,
    wherein the step of placing the apparatus in an operative position comprises situating the apparatus so that at least a part of the first bone part resides in the U-shaped receptacle,
wherein the base comprises a plate with a peripheral edge and the first length portion is coextensive with a portion of the peripheral edge, against the portion of the peripheral edge, and fixed relative to the portion of the peripheral edge.

Claim 3 should read:
3. A method of maintaining a position of a first bone part relative to a second bone part, the method comprising the steps of:
    a) obtaining an apparatus comprising a unitary body,
    the unitary body comprising: i) at least one elongate formed wire component with a length; and Signed and Sealed this
Seventeenth Day of September, 2024

Katherine Kelly Vidal
*Director of the United States Patent and Trademark Office*

CERTIFICATE OF CORRECTION (continued)
U.S. Pat. No. 11,986,227 B2 ii) a base,
  the at least one elongate formed wire component having a first length portion coextensive
    with, against, and fixed relative to, a portion of the base;
  b) placing the apparatus in an operative position wherein at least a portion of the at least one
    elongate formed wire component engages the first bone part; and
  c) with the apparatus in the operative position, anchoring the base to the second bone part to
    thereby fix the apparatus in the operative position,
  wherein the at least one elongate formed wire component defines a U-shaped receptacle,
  wherein the step of placing the apparatus in an operative position comprises situating the
    apparatus so that at least a part of the first bone part resides in the U-shaped
    receptacle,
  wherein the first length portion is welded to the base.

Claim 5 should read:
5. A method of maintaining a position of a first bone part relative to a second bone part, the method comprising the steps of:
  a) obtaining an apparatus comprising a unitary body,
the unitary body comprising: i) at least one elongate formed wire component with a length; and
    ii) a base,
  the at least one elongate formed wire component having a first length portion coextensive
    with, against, and fixed relative to, a portion of the base;
  b) placing the apparatus in an operative position wherein at least a portion of the at least one
    elongate formed wire component engages the first bone part; and
  c) with the apparatus in the operative position, anchoring the base to the second bone part to
    thereby fix the apparatus in the operative position,
  wherein the at least one elongate formed wire component defines a U-shaped receptacle,
  wherein the step of placing the apparatus in an operative position comprises situating the
    apparatus so that at least a part of the first bone part resides in the U-shaped
    receptacle,
  wherein the step of anchoring the base comprises anchoring the base using a fastener that is
    advanced into the second bone part to thereby draw the base towards the second bone
    part and thereby bear a length of the at least one elongate formed wire component
    against the second bone part.

Claim 6 should read:
6. A method of maintaining a position of a first bone part relative to a second bone part, the method comprising the steps of:
  a) obtaining an apparatus comprising a unitary body.
the unitary body comprising: i) at least one elongate formed wire component with a length; and
    ii) a base,
  the at least one elongate formed wire component having a first length portion coextensive
    with, against, and fixed relative to, a portion of the base;
  b) placing the apparatus in an operative position wherein at least a portion of the at least one
    elongate formed wire component engages the first bone part; and
  c) with the apparatus in the operative position, anchoring the base to the second bone part to thereby fix the apparatus in the operative position,
wherein the at least one elongate formed wire component defines a U-shaped receptacle,
wherein the step of placing the apparatus in an operative position comprises situating the apparatus so that at least a part of the first bone part resides in the U-shaped receptacle,
wherein the base comprises first and second pieces each fixed to the at least one elongate formed wire component and the step of anchoring the base comprises extending a fastener through each of the first and second pieces and into the second bone part.

Claim 7 should read:
7. An apparatus for maintaining a position of a first bone part relative to a second bone part, the apparatus comprising:
a unitary body,
the unitary body comprising: i) at least one elongate formed wire component with a length; and
ii) a base in the form of a first flat plate that is elongate with a length,
the at least one elongate formed wire component having a first length portion coextensive with the length of the first flat plate, against, and fixed relative to, a lengthwise portion of the first flat plate,
the apparatus configured: a) to be placed in an operative position wherein at least a portion of the
at least one elongate formed wire component can engage a first bone part; and b) so that upon a fastener being used to fix the base to a second bone part, the apparatus can be maintained in the operative position wherein associated first and second bone parts are maintained in a desired relationship,
wherein the first length portion is welded to the first flat plate.

Claim 9 should read:
9. An apparatus for maintaining a position of a first bone part relative to a second bone part, the apparatus comprising:
a unitary body,
the unitary body comprising: i) at least one elongate formed wire component with a length; and
ii) a base in the form of a first flat plate that is elongate with a length,
the at least one elongate formed wire component having a first length portion coextensive with the
length of the first flat plate, against, and fixed relative to, a lengthwise portion of the first flat plate,
the apparatus configured: a) to be placed in an operative position wherein at least a portion of the
at least one elongate formed wire component can engage a first bone part; and b) so that upon a fastener being used to fix the base to a second bone part, the apparatus can be maintained in the operative position wherein associated first and second bone parts are maintained in a desired relationship,
wherein the first flat plate has a peripheral edge and the first length portion is welded to the portion of the first flat plate at the peripheral edge.

CERTIFICATE OF CORRECTION (continued)
U.S. Pat. No. 11,986,227 B2

Claim 10 should read:

10. An apparatus for maintaining a position of a first bone part relative to a second bone part, the apparatus comprising:
- a unitary body,
- the unitary body comprising: i) at least one elongate formed wire component with a length; and
    - ii) a base in the form of a first flat plate that is elongate with a length,
- the at least one elongate formed wire component having a first length portion coextensive with the
    - length of the first flat plate, against, and fixed relative to, a lengthwise portion of the first flat plate, the apparatus configured: a) to be placed in an operative position wherein at least a portion of the
        - at least one elongate formed wire component can engage a first bone part; and b) so that upon a fastener being used to fix the base to a second bone part, the apparatus can be maintained in the operative position wherein associated first and second bone parts are maintained in a desired relationship,
- wherein the first flat plate defines the portion of the base with a bottom surface to face a bone portion to which the base is to be fixed and the first length portion extends to below the bottom surface.

Claim 11 should read:

11. An apparatus for maintaining a position of a first bone part relative to a second bone part, the apparatus comprising:
- a unitary body,
- the unitary body comprising: i) at least one elongate formed wire component with a length; and
    - ii) a base in the form of a first flat plate that is elongate with a length,
- the at least one elongate formed wire component having a first length portion coextensive with the
    - length of the first flat plate, against, and fixed relative to, a lengthwise portion of the first flat plate, the apparatus configured: a) to be placed in an operative position wherein at least a portion of the
        - at least one elongate formed wire component can engage a first bone part; and b) so that upon a fastener being used to fix the base to a second bone part, the apparatus can be maintained in the operative position wherein associated first and second bone parts are maintained in a desired relationship,
- wherein the first flat plate has a thickness and the first length portion has an effective diameter that is greater than or equal to the thickness of the first flat plate.